(12) United States Patent
Tsuboi et al.

(10) Patent No.: US 7,199,248 B2
(45) Date of Patent: Apr. 3, 2007

(54) PROCESS

(75) Inventors: Hiroyuki Tsuboi, Osaka (JP); Atsushi Ohigashi, Osaka (JP); Yoshitaka Shimojo, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 161 days.

(21) Appl. No.: 10/522,622

(22) PCT Filed: Aug. 4, 2003

(86) PCT No.: PCT/JP03/09900

§ 371 (c)(1),
(2), (4) Date: Jan. 31, 2005

(87) PCT Pub. No.: WO2004/014879

PCT Pub. Date: Feb. 19, 2004

(65) Prior Publication Data

US 2005/0227914 A1    Oct. 13, 2005

(30) Foreign Application Priority Data

Aug. 8, 2002  (JP) ............................. 2002-231182

(51) Int. Cl.
*C07D 261/08*    (2006.01)
*C07D 487/12*    (2006.01)

(52) U.S. Cl. ..................................... 548/247; 540/476
(58) Field of Classification Search ................ 548/247; 540/476

See application file for complete search history.

(56) References Cited

FOREIGN PATENT DOCUMENTS

WO    96 11210    4/1996

*Primary Examiner*—Kamal A. Saeed
*Assistant Examiner*—Michael P. Barker
(74) *Attorney, Agent, or Firm*—Oblon, Spivak, McClelland, Maier & Neustadt, P.C.

(57) ABSTRACT

The present invention relates to a process for preparing a pharmaceutical starting compound compound by hydrolyzing a compound of the general formula (II): Wherein $R^1$ is protected carboxy, $R^2$ is lower alkoxy or higher alkoxy, $A^1$ is an aromatic bivalent group, heterocyclic bivalent group or cyclo (lower) alkane bivalent group, and $A^2$ is an aromatic bivalent group, heterocyclic bivalent group or cyclo (lower) alkane bivalent group, with aqueous potassium hydroxide and by treating with hydrochloric acid.

(II)

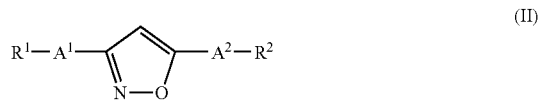

17 Claims, No Drawings

PROCESS

TECHNICAL FIELD

The present invention relates to a process for preparing a compound that is useful as an starting compound for producing an excellent antifungal agent and a process for preparing a excellent antifungal agent from the said starting compound.

BACKGROUND ART

International Patent Publication WO 96/11210 has disclosed a process (Preparation 31) for obtaining 4-[5-(4-pentyloxyphenyl)isoxazol-3-yl]benzoic acid as a starting compound for a lipopeptide antifungal agent and a process for preparing a excellent antifungal agent from the said starting compound.

DISCLOSURE OF INVENTION

In accordance with the process described in the above-mentioned International Patent Publication, 4-[5-(4-pentyloxyphenyl)isoxazol-3-yl]benzoic acid was obtained by hydrolyzing methyl 4-[5-(4-pentyloxyphenyl)isoxazol-3-yl]benzoate, a starting compound, with an aqueous sodium hydroxide, as described in Preparation 31. However, 5-(4-pentyloxyphenyl)-3-[4-[5-(4-pentyloxyphenyl)isoxazol-3-yl]phenyl]isoxazole was produced as a by-product in an initial step (Preparation 46) for producing the methyl 4-[5-(4-pentyloxyphenyl)isoxazol-3-yl]benzoate serving as the starting compound. It was difficult to isolate the 4-[5-(4-pentyloxyphenyl)isoxazol-3-yl]benzoic acid from the by-product. For this reason, the process was not preferable as a process for preparing the starting compound for a pharmaceutical product required having particularly high purity.

Hence, after earnest studies, the inventors of the present invention found a process capable of isolating the by-product, 5-(4-pentyloxyphenyl)-3-[4-[5-(4-pentyloxyphenyl) isoxazol-3-yl]phenyl]isoxazole, in the above-mentioned hydrolyzing process, thereby solving the problem encountered in the above-mentioned conventional hydrolyzing process.

The process of the present invention can be represented by the following reaction formulas.

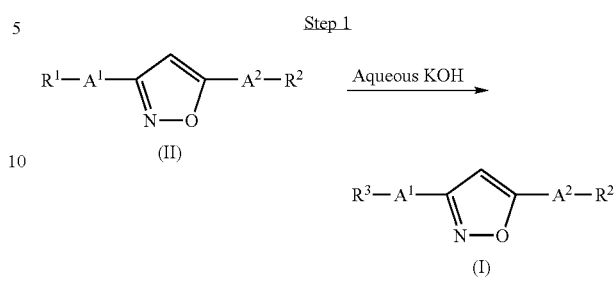

wherein $R^1$ is protected carboxy,
$R^2$ is lower alkoxy or higher alkoxy,
$R^3$ is a potassium salt of carboxy,
$A^1$ is an aromatic bivalent group, heterocyclic bivalent group or cyclo(lower)alkane bivalent group, and
$A^2$ is an aromatic bivalent group, heterocyclic bivalent group or cyclo(lower)alkane bivalent group.

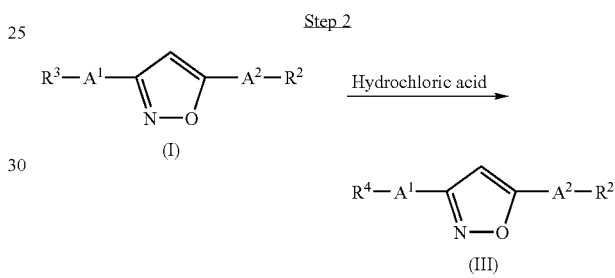

wherein $R^2$ is lower alkoxy or higher alkoxy,
$R^3$ is a potassium salt of carboxy,
$R^4$ is carboxy,
$A^1$ is an aromatic bivalent group, heterocyclic bivalent group or cyclo(lower)alkane bivalent group, and
$A^2$ is an aromatic bivalent group, heterocyclic bivalent group or cyclo(lower)alkane bivalent group.

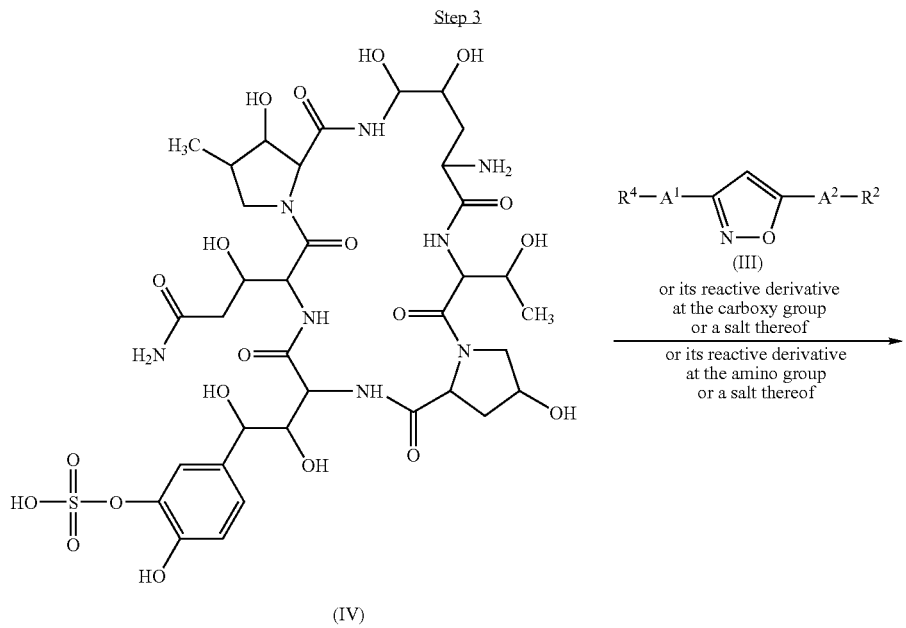

-continued

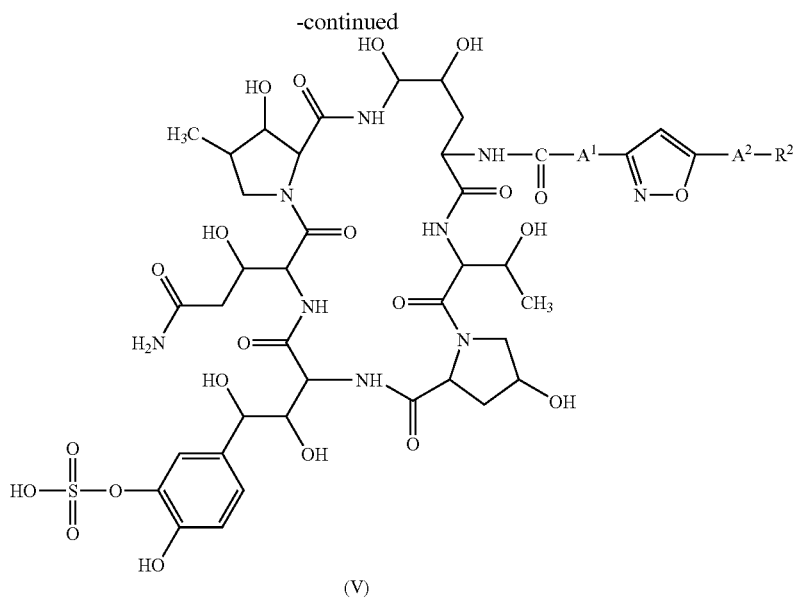

(V)

or a salt thereof
wherein R² is lower alkoxy or higher alkoxy,
R⁴ is carboxy,
A³ is an aromatic bivalent group, heterocyclic bivalent group or cyclo(lower)alkane bivalent group, and
A² is an aromatic bivalent group, heterocyclic bivalent group or cyclo(lower)alkane bivalent group.

This process is characterized in that the by-product is isolated by taking the step of producing the compound (I) from the starting compound (II). This compound (I) is novel.

Suitable examples and illustration of the various definitions in the above and subsequent descriptions of the present specification, which the present invention intends to include within the scope thereof, are explained in detail as follows:

The term "lower" is intended to mean 1 to 6 carbon atom(s), unless otherwise indicated.

The term "higher" is intended to mean 7 to 20 carbon atom(s), unless otherwise indicated.

Suitable "(lower)alkoxy" may include straight or branched one such as methoxy, ethoxy, propoxy, isopropoxy, butoxy, isobutoxy, sec-butoxy, t-butoxy, pentyloxy, isopentyloxy, neo-pentyloxy, t-pentyloxy, hexyloxy, isohexyloxy and the like, in which more preferable one may be ($C_3$–$C_6$) alkoxy and the most preferable one may be pentyloxy.

Suitable "higher alkoxy" may include straight or branched one such as heptyloxy, octyloxy, 5-dimethyloctyloxy, 3,7-dimethyloctyloxy, nonyloxy, decyloxy, undecyloxy, dodecyloxy, tridecyloxy, tetradecyloxy, hexadecyloxy, heptadecyloxy, octadecyloxy, nonadecyloxy, icosyloxy and the like.

Suitable "aromatic bivalent group" may be a bivalent group derived from benzene which may have lower alkyl (e.g. benzene, toluene, mesitylene, etc.), naphthalene, anthracene and the like, in which more preferable one may be phenylene.

Suitable "heterocyclic bivalent group" may be a bivalent group derived from:

unsaturated 3 to 8-membered (more preferably 5 or 6-membered) heteromonocyclic group containing 1 to 4 nitrogen atom(s), for example, pyrrolyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, piperidinyl, piperazinyl, etc.;

unsaturated condensed heterocyclic group containing 1 to 4 nitrogen atom(s), for example, indolyl, isoindolyl, indolizinyl, benzimidazolyl, quinolyl, dihydroquinolinyl, isoquinolinyl, indazolyl, quinoxalinyl, dihydroquinoxalinyl, benzotriazolyl, etc.;

unsaturated 3 to 8-membered (more preferably 5 or 6-membered) heteromonocyclic group containing 1 or 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 or 2 oxygen atom(s) and 1 to 3 nitrogen atom(s), for example, morpholinyl, sydnonyl, etc.;

unsaturated condensed heterocyclic group containing 1 or 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 or 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiadiazolyl, etc.;

saturated 3 to 8-membered (more preferably 5 or 6-membered) heteromonocyclic group containing 1 or 2 sulfur atom(s) and 1 to 3 nitrogen atom(s), for example thiazolidinyl, thiomorpholinyl, etc.;

unsaturated 3 to 8-membered (more preferably 5 or 6-membered) heteromonocyclic group containing 1 or 2 sulfur atom(s), for example, thiophenyl, dihydrothiophenyl, dihydrodithiophenyl, etc.

unsaturated condensed heterocyclic group containing 1 or 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl etc.;

unsaturated 3 to 8-membered (more preferably 5 or 6-membered) heteromonocyclic group containing an oxygen atom and 1 or 2 sulfur atom(s), for example, dihydrooxathiophenyl, etc.;

unsaturated condensed heterocyclic group containing 1 or 2 sulfur atom(s), for example, benzothiophenyl, benzodithiophenyl, etc.;

unsaturated condensed heterocyclic group containing an oxygen atom and 1 or 2 sulfur atom(s), for example, benzoxathiophenyl, etc.; and the like.

Suitable "cyclo(lower)alkane bivalent group" may be a bivalent group derived from cyclopropane, cyclobutane, cyclopentane, cyclohexane, etc.

Suitable "protected carboxy" may be a conventional one such as an esterified carboxy group, and concrete examples of the ester moiety in the esterified carboxy group may be such as lower alkyl ester [e.g. methyl ester, ethyl ester, propyl ester, isopropyl ester, butyl ester, isobutyl ester, t-butyl ester, pentyl ester, hexyl ester, 1-cyclopropylethyl ester, etc.], lower alkyl ester having a suitable substituent, e.g. lower alkanoyloxy(lower)alkyl ester [e.g. acetoxymethyl ester, propionyloxymethyl ester, butyryloxymethyl ester, valeryloxyethyl ester, pivaloyloxymethyl ester, 1-acetoxyethyl ester, 1-propionyloxyethyl ester, pivaloyloxyethyl ester, 2-propionyloxyethyl ester, hexanoyloxyethyl ester, etc.], lower alkanesulfonyl(lower)alkyl ester [e.g. 2-mesylethyl ester, etc.]or mono(or di or tri)halo(lower)alkyl ester [e.g. 2-iodoethyl ester, 2,2,2-trichloroethyl ester, etc.);

higher alkyl ester [e.g. heptyl ester, octyl ester, 3,5-dimethyloctyl ester, 3,7-dimethyloctyl ester, nonyl ester, decyl ester, undecyl ester, dodecyl ester, tridecyl ester, tetradecyl ester, pentadecyl ester, hexadecyl ester, heptadecyl ester, octadecyl ester, nonadecyl ester, adamantyl ester, etc.];

lower alkenyl ester [e.g. ($C_2$–$C_6$)alkenyl ester (e.g. vinyl ester, aryl ester, etc.)];

lower alkynyl ester [e.g. ($C_2$–$C_6$)alkynyl ester (e.g. ethynyl ester, propynyl ester, etc.)];

ar(lower)alkyl ester which may have one or more suitable substituent(s) [e.g. phenyl(lower)alkyl ester which may have 1 to 4 lower alkoxy, halogen, nitro, hydroxy; lower alkyl, phenyl or halo(lower)alkyl (e.g. benzyl ester, 4-methoxybenzyl ester, 4-chlorobenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, 4-trifluoromethylbenzyl ester, etc.)];

aryl ester which may have one or more suitable substituent (s) [e.g. aryl ester which may have 1 to 4 lower alkyl or halogen (e.g. phenyl ester, 4-chlorophenyl ester, tolyl ester, 4-t-butylphenyl ester, xylyl ester, mesityl ester, cumenyl ester, etc.)];

cycloalkyloxycarbonyloxy(lower)alkyl ester which may have lower alkyl (e.g. cyclopentyloxycarbonyloxymethyl ester, cyclohexyloxycarbonyloxymethyl ester, cycloheptyloxycarbonyloxymethyl ester, 1-methylcyclohexyloxycarbonyloxymethyl ester, 1-(or 2-)[cyclopentyloxycarbonyloxy]ethyl ester, 1-(or 2-)[cyclohexyloxycarbonyloxy] ethyl ester, 1-(or 2-)[cycloheptyloxycarbonyloxy]ethyl ester, etc.), etc.];

(5-(lower)alkyl-2-oxo-1,3-dioxol-4-yl)(lower)alkyl ester [e.g. (5-methyl-2-oxo-1,3-dioxol-4-yl)methyl ester, (5-ethyl 2-oxo-1,3-dioxol-4-yl)methyl ester, (5-propyl-2-oxo-1,3-dioxol-4-yl)methyl ester, 1-(or 2-)(5-methyl-2-oxo-1,3-dioxol-4-yl)ethyl ester, 1-(or 2-)(5-ethyl-2-oxo-1,3-dioxol-4-yl)ethyl ester, 1-(or 2-)(5-propyl-2-oxo-1,3-dioxol-4-yl)ethyl ester, etc.]; or the like.

Among them, preferable one may be lower alkyl ester, lower alkanoyloxy(lower)alkyl ester, ar(lower)alkyl ester which may have one or more suitable substituent(s), cycloalkyloxycarbonyloxy(lower)alkyl ester which may have lower alkyl, higher alkyl ester and (5-(lower)alkyl-2-oxo-1,3-dioxol-4-yl)(lower)alkyl ester, more preferable one may be lower alkyl ester, and the most preferable one may be methyl ester.

A preferable embodiment in accordance with the present invention is a process for using the compound (II) as a starting compound, in which $R^1$ is lower alkoxy carbonyl, $R^2$ is lower alkoxy, $A^1$ is an aromatic bivalent group, and $A^2$ is an aromatic bivalent group, most preferably, $R^1$ is methoxy carbonyl, $R^2$ is pentyloxy, $A^1$ is phenylene and $A^2$ is phenylene.

The process in accordance with the present invention will be explained below in detail.

Step 1

The compound (I) can be prepared by hydrolyzing the compound (II) with aqueous potassium hydroxide.

This reaction is usually carried out in a solvent which does not adversely affect the reaction, such as water, alcohol (e.g. methanol, ethanol, propanol, etc.), benzene, N,N-dimethylformamide, dimethyl sulfoxide, tetrahydrofuran, toluene, methylene chloride, ethylene dichloride, chloroform, 1,2-dimethoxy ethane, dioxane, diethyl ether, etc., or the mixture thereof.

The reaction temperature is not critical, and the reaction is usually carried out at room temperature or under warming or heating. The temperature is preferably 20 to 80° C., and more preferably 50 to 60° C.

Step 2

The compound (III) can be prepared by reacting the compound (I) with hydrochloric acid.

This reaction is usually carried out in a solvent which does not adversely affect the reaction, such as water, alcohol (e.g. methanol, ethanol, propanol, etc.), benzene, N,N-dimethylformamide, dimethyl sulfoxide, tetrahydrofuran, toluene, methylene chloride, ethylene dichloride, chloroform, 1,2-dimethoxy ethane, dioxane, ethyl acetate, diethyl ether, etc., or the mixture thereof.

The reaction temperature is not critical, and the reaction is usually carried out at room temperature or under warming or heating. The temperature is preferably 20 to 60° C., and more preferably 25 to 55° C.

Step 3

The compound (V) or a salt thereof can be prepared by reacting compound (III) or its reactive derivative at the carboxy group or a salt thereof with the compound (IV) or its reactive derivative at the amino group or salt a thereof.

This compound (III) can be converted into its reactive derivative at the carboxy group or a salt thereof in a conventional manner.

Suitable reactive derivative of the compound (III) may include an acid halide, an acid anhydride, an activated ester, and the like. The suitable example may be an acid chloride; acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.); aromatic carboxylic acid (e.g., benzoic acid, etc.); a symmetrical acid anydride; an activated amide with imidazole, 4-substituted imidazole, dimethylpyrazole, triazole or tetrazole; an activated ester (e.g., cyanomethyl ester methoxymethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthioester, p-nitrophenyl thioester, p-cresyl thioester, carboxymethyl thioester, pyranyl ester, pyridyl ester, piperidyl ester, 8-quinolyl thioester, etc.); an ester with a N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which do not adversely affect the reaction, or the mixture thereof.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide); N-cyclohexyl-N'-(4-diethylaminocyclohexyl)carbodiimide; N,N'-diisopropylcarboxiimide; N-ethyl-N'-(3-dimethylaminopropyl)carbodiimide; N,N-carbonyl-bis(2-methylimidazole); pentamethyleneketene-N-cyclohexylimine; diphenylketene-N-cyclohexylimine, ethoxyacetylene; 1-alkoxy-1-chloroethylene; trialkyl phosphite; isopropyl polyphosphate; phosphorous oxychloride (phosphoryl chloride); phosphorous trichloride; thionyl chloride; oxalyl chloride; triphenylphosphite; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorous oxychloride, etc.; or the like.

The reaction may also be carried out in the presence of an organic or inorganic base such as an alkali metal bicarbonate, tri(lower)alkylamine (e.g., triethylamine, diisopropylethylamine, etc.), pyridine, di(lower)alkylaminopyridine (e.g., 4-dimethylaminopyridine, etc.) N-(lower)alkylmorphorine, N,N-di(lower)alkylbenzylamine, or the like.

The reaction temperature is not critical, and the reaction is usually carried out under cooling to heating.

The compounds (I), (III) and (V) obtained by the process of the present invention can be isolated and purified by a conventional method such as pulverization, recrystallization, column-chromatography, reprecipitation or the like.

It is to be noted that the compounds (I), (III) and (V) obtained by the process of the present invention may include one or more stereoisomer(s) such as optical isomer(s) and geometrical isomer(s) due to asymmetric carbon atom(s) and double bond(s) and all such isomers and mixtures thereof are also included within the scope of the present invention.

In accordance with the known process (International Patent Publication WO 96/11210), it was difficult to isolate the by-product, 5-(4-pentyloxyphenyl)-3-[4-[5-(4-pentyloxyphenyl)isoxazol-3-yl]phenyl]isoxazole, from 4-[5-(4-pentyloxyphenyl)isoxazol-3-yl]benzoic acid. However, in accordance with the process of the present invention, the by-product can be isolated from the compound (I) owing to the difference in solubility in a solvent between the by-product and the compound (I). Hence, the compounds (III) having high purity can be obtained at a high yield. The process is thus useful as an industrial process for preparing pharmaceutical products required to have a particularly high purity.

The following Examples are given for the purpose of illustrating the present invention specifically.

EXAMPLE 1

Methyl 4-[5-(4-pentyloxyphenyl)isoxazol-3-yl]benzoate (16.4 kg), tetrahydrofuran (164 L), methanol (25 L) and 19% aqueous potassium hydroxide (25 L) were put into a 1500 L glass-lined reaction chamber, heated to 50 to 60° C., and stirred for 2 hours. Tetrahydrofuran (328 L) was added to this reaction mixture for 30 minutes to 1 hour. The mixture was then cooled to 35 to 40° C. and stirred further for 1 hour. The product was isolated by a centrifugal separator and washed with tetrahydrofuran (164 L) to obtain rough potassium 4-[5-(4-pentyloxyphenyl)isoxazol-3-yl]benzoate (which was used in the next step in a wet state).

EXAMPLE 2

The rough potassium 4-[5-(4-pentyloxyphenyl)isoxazol-3-yl]benzoate obtained in Example 1 in the wet state and tetrahydrofuran (328 L) were put into a 1500 L glass-lined reaction chamber, heated to 50 to 60° C., and stirred for 20 to 30 minutes. This reaction mixture was cooled to 35 to 40° C. and stirred further for 1 hour. The product was isolated by a centrifugal separator and washed with tetrahydrofuran (164 L) to obtain pure potassium 4-[5-(4-pentyloxyphenyl) isoxazol-3-yl]benzoate.

NMR (DMSO-$d_6$, δ): 0.91 (3H, t, J=7.0 Hz), 1.3–1.5 (4H, m), 1.6–1.8 (2H, m), 4.05 (2H, t, J=6.5 Hz), 7.11 (2H, d, J=8.6 Hz), 7.43 (1H, s), 7.76 (2H, d, J=8.3 Hz), 7.84(2H, d, J=8.7 Hz), 7.92 (2H, d, J=8.3 Hz)

EXAMPLE 3

The pure potassium 4-[5-(4-pentyloxyphenyl)isoxazol-3-yl]benzoate obtained in Example 2, tetrahydrofuran (131 L) and water (131 L) were put into a 1000 L glass-lined reaction chamber, heated to 45 to 55° C., and 1N hydrochloric acid (82 L) was added to this reaction mixture for 20 or more minutes. Furthermore, water (607 L) was added to the reaction mixture for 30 or more minutes at the same temperature. This reaction mixture was cooled to 25 to 35° C. and its pH was adjusted to 3 or less with 6N hydrochloric acid. The product was isolated by a centrifugal separator and washed with water (164 L) and acetone (82 L) and dried by a vacuum drier to obtain pure 4-[5-(4-pentyloxyphenyl) isoxazol-3-yl]benzoic acid (14.9 kg).

NMR (DMSO-$d_6$, δ): 0.91 (3H, t, J=7.1 Hz), 1.3–1.5 (4H, m), 1.6–1.8 (2H, m), 4.04 (2H, t, J=6.5 Hz), 7.11 (2H, d, J=8.9 Hz), 7.54 (1H, s), 7.85 (2H, d, J=8.9 Hz), 7.98 (2H, d, J=8.6 Hz), 8.11 (2H, d, J=8.6 Hz)

The ratio of the by-product, 5-(4-pentyloxyphenyl)-3-[4-[5-(4-pentyloxyphenyl)isoxazol-3-yl]phenyl]isoxazole, included in the pure 4-[5-(4-pentyloxyphenyl)isoxazol-3-yl]benzoic acid was less than 0.05% in the process of the present invention, in comparison with 0.80% in the conventional process. The ratio was therefore reduced significantly.

EXAMPLE 4

4-[5-(4-pentyloxyphenyl)isoxazol-3-yl]benzoic acid (14.7 kg) obtained in Example 3, tetrahydrofuran (147 L), dimethylformamide (118 L) and 1-hydroxybenzotriazole (7.9 kg) were added at 20–25° C. to a 1500-L glass-lined vessel. And then, 1-ethyl-3-(3'-dimethylaminopropyl)carbodiimide hydrochloride (13.6 kg) was added and stirred for 3 hours at this temperature. The reaction mixture was cooled to below 10° C., and then ethyl acetate (480 L) and water (120 L) were added dropwise at below 25° C. After cooling to 2–7° C., the slurry was stirred for 1 hour at this temperature. The product was collected on a stainless centrifuge and washed with acetonitrile (74 L). The damp solid was dried in a stainless vacuum dryer under vacuum to give 1-[4-[5-(4-pentyloxyphenyl)isoxazol-3-yl]benzoyloxy]-1H-1,2,3-benzotriazole (18.6 kg).

EXAMPLE 5

N,N-dimethyl formamide (167 L) and the starting compound (5) as shown below (15.00 kg) were mixed in a 500-L vessel. The mixture was stirred at −5 to 20° C. to dissolve completely. N,N-diisopropyl ethylamine (3.19 kg) was added to the solution at the same temperature. The mixture was cooled to −8 to 10° C. and then 1-[4-[5-(4-pentyloxyphenyl)isoxazol-3-yl]benzoyloxy]-1H-1,2,3-benzotriazole (8.18 kg) was added. The reaction mixture was stirred for 2.0 to 4.0 hours at −3 to 10° C. to give the crude object compound (5) as shown below. (which was used in the next step in a wet state)

EXAMPLE 6

Ethyl acetate (1080 L) was added to the crude object compound (5) obtained in Example 5 for 1.5 to 2.5 hours at 0 to 40° C. in a 5000-L vessel. The resulting slurry for more than 1 hour at 0 to 15° C. The slurry was filtered on a 1200-L hastelloy C-22 pressure filter. The wet of the object compound (5) was washed with ethyl acetate (400 L) and then compressed. Acetone (53 L) and ethyl acetate (105 L) were added to the resulting cake. The resulting cake and methanol (225 L) were mixed in a 1200-L hastelloy C-22 pressure filter. The mixture was stirred at 5 to 40° C. to dissolve completely. The solution was passed through regenerated γ Alumina (458 L) in a 1350-L column. The object compound (5) was then eluted with methanol (2500 L). The fraction containing the object compound (5) was charged in a 3000-L vessel. The fraction was concentrated to approximately 180 L under vacuum below 30° C. in a 1500-L vessel. The resultant residue and purified water (54 L) were mixed. The solution was heated to 10 to 40° C., and was passed through regenerated ion exchange resin UBK510L (330 L) to obtain the object compound (6) in a 830-L column. The object compound (6) was eluted with aqueous methanol (methanol/water=75/25). The fraction was collected until the concentration of the object compound (6) was not less than 31 g/L. The pH of the solution was controlled (pH range: 6 to 8), and then 0.1 mol/L-sodium hydroxide solution was added to the fraction in a 5000-L vessel. Ethyl acetate (600 L) was added to the resulting solution. Acetone (1313 L) and ethyl acetate (1313 L) were mixed in a 3000-L vessel. The mixed solvent [acetone/ethyl acetate]was added to the fraction for precipitation of the object compound (6) at 0 to 10° C. for 4 to 5.5 hours in a 5000-L vessel. The resulting slurry was stirred for more than 3 hours at the same temperature. The wet object compound (6) was dried under vacuum for 15 to 48 hours below 40° C. to give approximately 16.3 kg of the object compound (6) as shown below.

IR (KBr): 3350, 2935, 2873, 1668, 1629, 1538, 1506, 1438, 1257, 1049 cm$^{-1}$

NMR (DMSO-$d_6$, δ): 0.9–1.0 (6H, m), 1.08 (3H, d, J=5.7 Hz), 1.2–1.6 (4H, m), 1.6–2.0 (5H, m), 2.1–2.4 (3H, m), 2.5–2.6 (1H, m), 3.1–3.2 (1H, m), 3.6–4.6 (15H, m), 4.7–5.2 (10H, m), 5.26 (1H, d, J=4.5 Hz), 5.55 (1H, d, J=5.9 Hz), 6.7–6.9 (3H, m), 7.0–7.6 (7H, m), 7.85 (2H, d, J=8.6 Hz), 7.9–8.2 (4H, m), 8.26 (1H, d, J=7.7 Hz), 8.8–9.0 (2H, m)

Starting compound (5)

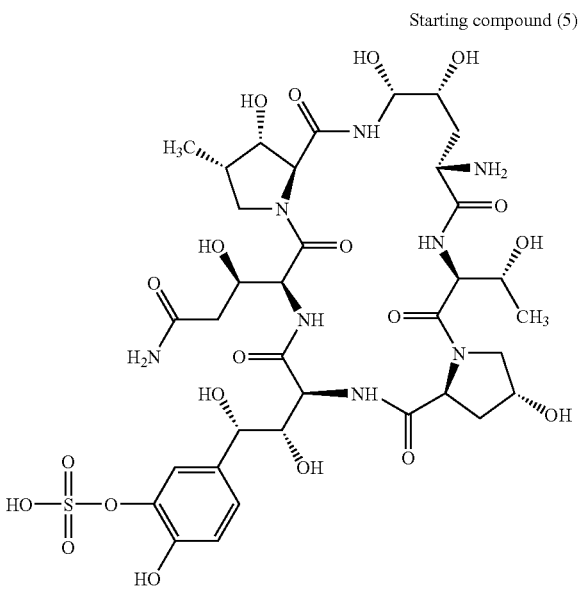

Object compound (5)

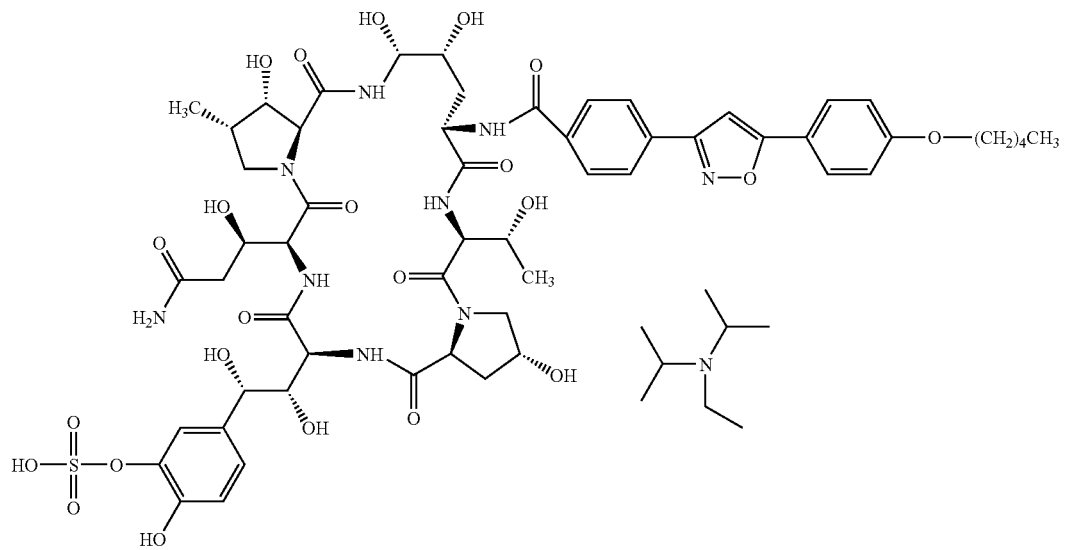

Object compound (6)

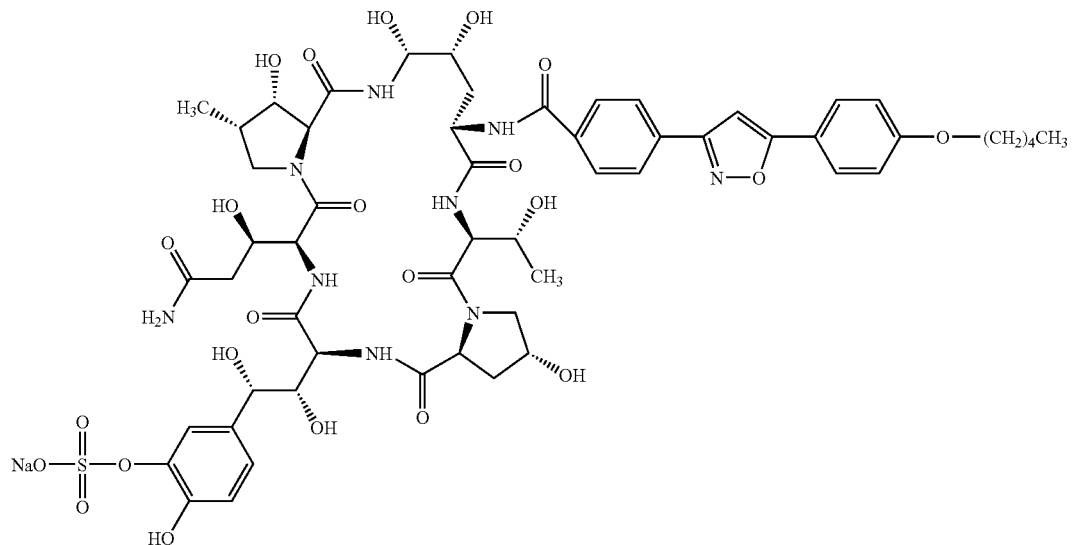

The invention claimed is:

1. A process for preparing a compound of the formula (III):

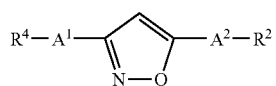

wherein $R^2$ is lower alkoxy or higher alkoxy,
$R^4$ is carboxy
$A^1$ is an aromatic bivalent group, heterocyclic bivalent group or cyclo(lower)alkane bivalent group, and
$A^2$ is an aromatic bivalent group, heterocyclic bivalent group or cyclo(lower)alkane bivalent group, which comprises:

hydrolyzing a compound of the general formula (II):

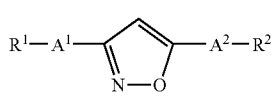

wherein $R^2$, $A^1$ and $A^2$ are each as defined above, and—

$R^1$ is protected carboxy, with aqueous potassium hydroxide to give a compound of the general formula (I):

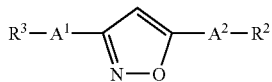 (I)

wherein $R^2$, $A^1$ and $A^2$ are each as defined above, and
$R^3$ is a potassium salt of carboxy, and reacting this compound (I) with hydrochloric acid to obtain the compound (III).

2. A process of claim 1, wherein
$R^2$ is lower alkoxy,
$A^1$ is an aromatic bivalent group or heterocyclic bivalent group, and
$A^2$ is an aromatic bivalent group or heterocyclic bivalent group.

3. A process of claim 2, wherein
$A^1$ is an aromatic bivalent group, and
$A^2$ is an aromatic bivalent group.

4. A process of claim 3, wherein
$A^1$ is phenylene, and
$A^2$ is phenylene.

5. A process for preparing a compound of the formula (I):

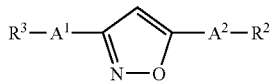 (I)

wherein $R^2$ is lower alkoxy or higher alkoxy,
$R^3$ is a potassium salt of carboxy,
$A^1$ is an aromatic bivalent group, heterocyclic bivalent group or cyclo(lower)alkane bivalent group, and
$A^2$ is an aromatic bivalent group, heterocyclic bivalent group or cyclo(lower)alkane bivalent group,
which comprises:
hydrolyzing a compound of the general formula (II):

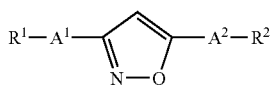 (II)

wherein $R^2$, $A^1$ and $A^2$ are each as defined above, and
$R^1$ is protected carboxy,
with aqueous potassium hydroxide to give the compound (I).

6. A process of claim 5, wherein
$R^2$ is lower alkoxy,
$A^1$ is an aromatic bivalent group or heterocyclic bivalent group, and
$A^2$ is an aromatic bivalent group or heterocyclic bivalent group.

7. A process of claim 6, wherein
$A^1$ is an aromatic bivalent group, and
$A^2$ is an aromatic bivalent group.

8. A process of claim 7, wherein
$A^1$ is phenylene, and
$A^2$ is phenylene.

9. A process for preparing a compound of the formula (III):

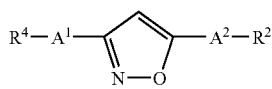 (III)

wherein $R^2$ is lower alkoxy or higher alkoxy,
$R^4$ is carboxy
$A^1$ is an aromatic bivalent group, heterocyclic bivalent group or cyclo(lower)alkane bivalent group, and
$A^2$ is an aromatic bivalent group, heterocyclic bivalent group or cyclo(lower)alkane bivalent group,
which comprises:
reacting a compound of the general formula (I):

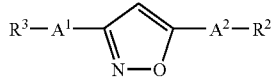 (I)

wherein $R^2$, $A^1$ and $A^2$ are each as defined above, and
$R^3$ is a potassium salt of carboxy,
with hydrochloric acid to obtain the compound (III).

10. A process of claim 9, wherein
$R^2$ is lower alkoxy,
$A^1$ is an aromatic bivalent group or heterocyclic bivalent group, and
$A^2$ is an aromatic bivalent group or heterocyclic bivalent group.

11. A process of claim 10, wherein
$A^1$ is an aromatic bivalent group, and
$A^2$ is an aromatic bivalent group.

12. A process of claim 11, wherein
$A^1$ is phenylene, and
$A^2$ is phenylene.

13. A process for preparing a compound of the formula (V):

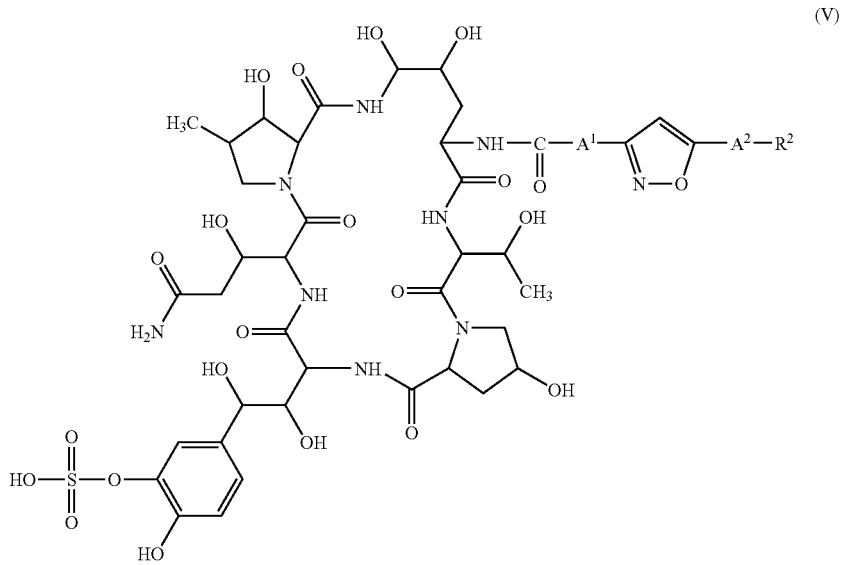

wherein $R^2$ is lower alkoxy or higher alkoxy,
$A^1$ is an aromatic bivalent group, heterocyclic bivalent group or cyclo(lower)alkane bivalent group, and
$A^2$ is an aromatic bivalent group, heterocyclic bivalent group or cyclo(lower)alkane bivalent group, or salt thereof,
which comprises:
hydrolyzing a compound of the general formula (II):

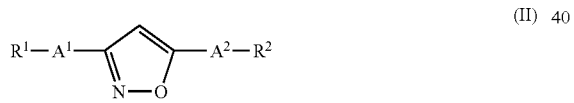

wherein $R^2$, $A^1$ and $A^2$ are each as defined above, and $R^1$ is protected carboxy,
with aqueous potassium hydroxide to give a compound of the general formula (I):

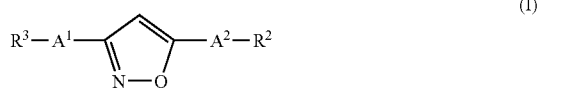

wherein $R^2$, $A^1$ and $A^2$ are each as defined above, and $R^3$ is a potassium salt of carboxy,
and reacting this compound (I) with hydrochloric acid to give the compound of the general formula (III):

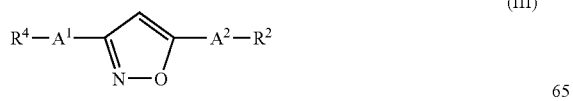

wherein $R^2$ $A^1$ and $A^2$ are each as defined above, and $R^4$ is carboxy, and if necessary, converting the compound (III) into its reactive derivative at the carboxy group or a salt thereof in a conventional manner,
and reacting the compound (III) or its reactive derivative at the carboxy group or a salt thereof with the compound of the formula (IV):

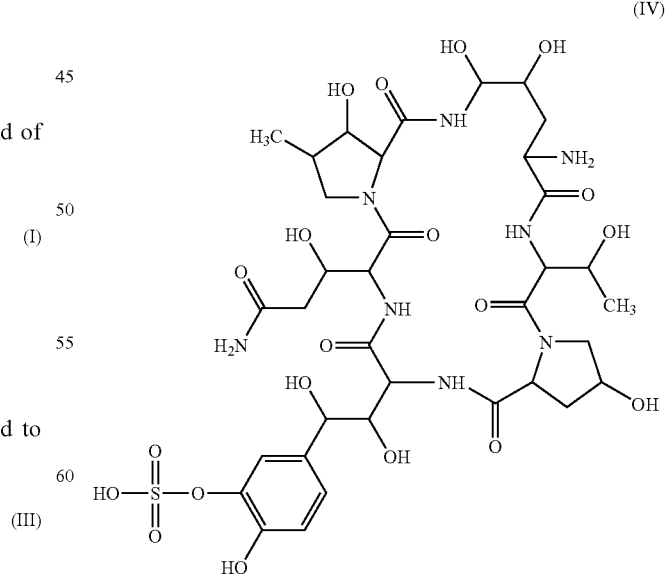

or its reactive derivative at the amino group or a salt thereof to obtain the compound (V) or a salt thereof.

14. A process of claim 13, wherein $R^2$ is lower alkoxy, $A^1$ is an aromatic bivalent group or heterocyclic bivalent group, and $A^2$ is an aromatic bivalent group or heterocyclic bivalent group.

15. A process of claim 14, wherein $A^1$ is an aromatic bivalent group, and $A^2$ is an aromatic bivalent group.

16. A process of claim 15, wherein $A^1$ is phenylene, and $A^2$ is phenylene.

17. A process of claim 1, wherein formula (III) is 4-[5-(4-pentyloxyphenyl)isoxazol-3-yl]benzoic acid.

* * * * *